US005776459A

United States Patent [19]
Vandenbark

[11] Patent Number: 5,776,459
[45] Date of Patent: *Jul. 7, 1998

[54] TCR V BETA 5 PEPTIDES

[75] Inventor: Arthur A. Vandenbark, Portland, Oreg.

[73] Assignee: Connetics Corporation, Palo Alto, Calif.

[*] Notice: The term of this patent shall not extend beyond the expiration date of Pat. No. 5,614,192.

[21] Appl. No.: 476,405

[22] Filed: Jun. 7, 1995

Related U.S. Application Data

[63] Continuation-in-part of Ser. No. 59,020, Mar. 16, 1993, Pat. No. 5,614,192, which is a continuation of Ser. No. 735,612, Jul. 16, 1991, abandoned, which is a continuation-in-part of Ser. No. 708,022, May 31, 1991, abandoned, which is a continuation-in-part of Ser. No. 554,529, Jul. 19, 1990, abandoned, which is a continuation-in-part of Ser. No. 467,577, Jan. 19, 1990, abandoned, which is a continuation-in-part of Ser. No. 382,804, Jul. 19, 1989, abandoned.

[51] Int. Cl.$^6$ .................. A61K 38/00; C07K 14/725
[52] U.S. Cl. ........................ 424/185.1; 424/185.1; 424/193.1; 530/326; 530/328; 530/300; 530/395; 530/868
[58] Field of Search .................. 530/326–8, 300, 530/395, 403, 868; 424/185.1, 193.1

[56] References Cited

U.S. PATENT DOCUMENTS

| | | |
|---|---|---|
| 4,634,590 | 1/1987 | Cohen et al. . |
| 4,716,038 | 12/1987 | Stanford et al. . |
| 4,845,026 | 7/1989 | Kung et al. . |
| 4,873,190 | 10/1989 | Saito et al. . |
| 4,874,845 | 10/1989 | Saito et al. . |
| 4,886,743 | 12/1989 | Hood et al. . |
| 5,316,925 | 5/1994 | Davis et al. . |
| 5,340,921 | 8/1994 | Brenner et al. . |
| 5,612,035 | 3/1997 | Howell et al. ............. 424/185.1 |
| 5,614,192 | 3/1997 | Vandenbark ............. 424/185.1 |

FOREIGN PATENT DOCUMENTS

| | | |
|---|---|---|
| 1197480 | 12/1985 | Canada . |
| 0291046 | 11/1988 | European Pat. Off. . |
| 0296786 | 12/1988 | European Pat. Off. . |
| 0304279 | 2/1989 | European Pat. Off. . |
| 0340109 | 11/1989 | European Pat. Off. . |
| 0403156 | 12/1990 | European Pat. Off. . |
| 8606413 | 11/1986 | WIPO . |
| 8703600 | 6/1987 | WIPO . |
| WO 90/11294 | 10/1990 | WIPO . |
| 9117268 | 11/1991 | WIPO . |
| 92/13950 | 8/1992 | WIPO ............. C12N 15/12 |
| WO 93/12814 | 7/1993 | WIPO . |
| 9508572 | 3/1995 | WIPO . |

OTHER PUBLICATIONS

Hafler, D.A. et al., Immunology Today 17(4):152–159 (Apr., 1996), "TCR usage in human and experimental demyelinating disease".

Kumar, V et al., PNAS 87:1337–1341, Amino acid variations at a single residue in an autoimmune peptide profoundly affect is properties: T–cell activation, major histcompatibility complex binding, and ability to block experimental allergic encephalomyelit, Feb. 1990.
Hood, L. et al., PNAS 88:6899 "Clarification and retraction", Aug. 1, 1991.
Chothia, C. et al., EMBO J. 7:3745–3755, "The outline structure of the T–cell alpha–beta receptor", 1988.
Robinson, M. A. et al., pp. 269–287 in T cell Receptors (John I. Bell et al., eds), Oxford Univ. Press, Oxford, UK 1995.
Acha–Orbea et al., "Limited heterogeneity of T cell receptors from lymphocytes mediating autoimmune encephalomyelitis specific immune intervention", *Cell* 54:263–273 (1988).
Acha–Orbea et al., "T Cell Receptors in Murine Autoimmune Diseases", *Ann. Rev. Immunol.* 7:371–405 (1989).
Allegretta et al., "T Cells Responsive to Myelin Basic Protein in Patients with Multiple Sclerosis", *Science* 247:718–721 (1990).
Alvord et al., *Exp. Allergic Encephalomyelitis*, A.R. Liss Publisher, New York, pp. 523–537 (1984).
Barth et al., "The Murine T–Cell Receptor Uses A Limited Repertoire of Expressed V βGene Segments", *Nature* 316:517–523 (1985).
Beall et al., *J. Neuroimmunol.* 21:59–66 (1989).
Ben–Nun et al., "Vaccination against autoimmune encephalomyelitis with T–lymphocyte line cells reactive against myelin basic protein", *Nature* 292:60–61 (1981).
Ben–Nun et al., "The Rapid Isolation of Clonable Antigen–Specific T Lymphocyte Lines Capable of Mediating Autoimmune Encephalomyelitis", *European Journal of Immunology* 11:195–199 (1981).
Berzofsky, "T–Cell Activation by Antigen: Promising Clues to Reception Genes and Molecules", *Immunology Today* 4:299–301 (1983).
Bourdette et al., "Immunity to TCR Peptides in Multiple Sclerosis", *Amer. Assoc. of Immunol.* pp. 2510–2519 (1994).
Bourdette et al., *J. Neuroimmunol.* 26:81–85 (1990).
Bourdette et al., "Basic Protein–Specific T–Cell Lines That Induce Experimental Autoimmune Encephalomyelitis in SLJ/J Mice: Comparison with Lewis Rat Lines", *Cell. Immunol.* 112:351–363 (1988).
Bourdette et al., "Immunity to TCR Peptides in Multiple Sclerosis I. Successful Immunization of Patients With Synthetic Vβ5.2 and Vβ6.1 CDR2 Peptides", *J. Immunol.* 152:2510–2519 (1994).
Brostoff et al., "Vaccination with T–cell receptor peptides", *Immunol. Ser.* 59:203–218 (1993).

(List continued on next page.)

*Primary Examiner*—Thomas M. Cunningham
*Attorney, Agent, or Firm*—David A. Lowin, Esq.

[57] ABSTRACT

TCR peptides from the Vβ5 family, particularly those encompassing at least a part of the second complementarity determining region, are useful, e.g., in the diagnosis and treatment of multiple sclerosis.

27 Claims, No Drawings

OTHER PUBLICATIONS

Brostoff et al., *J. Neuroimmunol.* 13:233–240 (1986).

Burns et al., "Both Rat and Mouse T Cell Receptors Specific for the Encephalitogenic Determinant of Myelin Basic Protein Use Similar Vα and VβChain Genes Even Though the Major Histocompatibility Complex and Encephalitogenic Determinants Being Recognized are Different", *J. Exp. Med.* 169:27–39 (1989).

Chluba et al., "T cell receptor β chain usage in myelin basic protein–specific rat T–lymphocytes", *Europ. J. Immunol.* 19:279–284 (1989).

Chou et al., "Immunity to TCR Peptides in Multiple Sclerosis", *J. Immunol.* 152:2520–2529 (1994).

Chou et al., *J. of Neurochem.* 28:115–119 (1977).

Chou et al., "Selection of Encephalitogenic Rat T Lymphocyte Clones Recognizing and Immunodominant Epitope on Myelin Basic Protein", *J. Neurosci. Res.* 22:181–187 (1989).

Chou et al., *J. Neurosci. Res.* 23:207–216 (1989).

Clark et al., "Identification of a Diversity Segment of Human T–Cell Receptor β–Chain, and Comparison with the Analogous Murine Element", *Nature* 311:387–389 (1984).

Claverie et al., "Implications of a Fab–Like Structure for the T–Cell Receptor", *Immunol. Today* 10:10–14 (1989).

Clevers et al., "The T–Cell Receptor/CD3 Complex: A Dynamic Protein Ensemble", *Annual Review of Immunology* 6:629–662 (1988).

Cohen, "Regulation of Autoimmune Disease Physiological and Therapeutic", *Immunol. Rev.* 94:5–21 (1986).

Cohen, *Hosp. Prac.* pp. 57–64 (1989).

Cohen et al., *Cell Imm.* 108:203–213 (1987).

Cohen, *Prog. Immunol.* VI:491–499 (1986).

Cohen and Weiner, "T–Cell Vaccination", *Immunology Today* 9:332–335 (1988).

Desquenne–Clark et al., "T–cell receptor peptide immunization leads to enhanced and chronic experimental allergic encephalomyeleitis", *Proc. Natl. Acad. Sci. USA* 88:7219–7233 (1991).

Esch et al., "Observations, Legends and Conjectures Concerning Restricted T–Cell Receptor Usage and Autoimmune Disease", *Critical Reviews in Immunology* 11(5):249–264 (1992).

Eylar et al., "Basic A1 Protein of the Myelin Membrane", *J. Biol. Chem.* 246(18):5770–5784 (1971).

Ford et al., *Cell. Immunol.* 79:334–344 (1983).

Gammon et al., *Immunol. Rev.* 98:53–73 (1987).

Gascoigne et al., "Secretion of a Chimeric T–Cell Receptor–Immunoglobulin Protein", *Proc. Natl. Acad. Sci. USA* 84:2936–2940 (1987).

Gaur et al., "Requirement for DC8+ Cells in T Cell Receptor Peptide–Induced Clonal Unresponsiveness", *Science* 259:91–93 (1993).

Geha, *Clin. Immunol. and Immunopath.* 19:196–205 (1981).

Hafler et al., *J. Immunol.* 139(1):68–72 (1987).

Happ et al., *J. Neuroimmunol.* 19:191–204 (1988).

Hashim et al., "Suppression of autoimmunity by antibodies against synthetic T cell receptor peptides", *FASEB Journal* 4(7):A2023 (1990).

Hashim et al., "Biological Activity of Region 65–102 of the Myelin Basic Protein", *J. Neurosci. Res.* 24:222–230 (1989).

Hashim et al., *J. Immunol.* 144(12):4621–4627 (1990).

Herber–Katz et al., "The V–region disease hypothesis: evidence from autoimmune encephalomyleitis", *Immunol. Today* 10:164–169 (1989).

Heber–Katz et al., "Clonal Modulation of Experimental Allergic Encephalomyelitis by a Monoclonal Antibody Directed to the T–Cell Receptor", *Advances in Neuroimmunology* 540:576–577 (1988).

Higgins et al., *J. Immunol.* 140(2):440–445 (1988).

Holoshitz et al., "Autoimmune encephalomyelitis (EAE) mediated or prevented by T lymohocyte lines directed against diverse antigenic determinants if myelin basic protein. Vaccination is determinant specific", *J. Immunol.* 131:2810–2813 (1983).

Howell et al., "Vaccination against experimental allergic encephalomyelitis with T cell receptor peptides", *Science* 246:688–670 (1989).

Janeway, *Nature* 341:482–483 (1989).

Kappler et al., *Science* 244:811–813 (1989).

Kappler et al., "Self–Tolerance Eliminates T Cells Specific for MIs–Modified Products oft the Major Histocompatibility Complex", *Nature* 332:35–40 (1988).

Kappler et al., "A T Cell receptor $V_{beta}$ segment that imparts reactivity to a class II major histocompatibility complex product", *Cell* 49:263–271 (1987).

Karpus et al., "CD4+ Suppressor Cells of Autoimmune Encephalomyelitis Respond to T Cell Receptor–Associated Determinants of Effector Cells by Interleukin–4 Secretion", *Eur. J. Immunol.* 22:1757–1763 (1992).

Kitzin et al., "Preferential T–cell receptor beta–chain variable gene uise in myelin basic protein reactive T–cell clones from patients with multiple sclerosis," *Proc. Natl. Acad. Sci. USA* 88:9161–9165 (1991).

Kotzin et al., "Preferential T–Cell Receptor β–Chain Variable Gene Use in Myelin Basic Protein–Reactive T–Cell Clones From Patients With Multiple Sclerosis," *Proc. Natl. Acad. Sci. USA* 88:9161–9165 (1991).

Kumar et al., "The Involvement of T Cell Receptor Peptide–Specific Regulatory CD4+ T Cells in Recovery From Antigen–Induced Autoimmune Disease," *J. Exp. Med.* 178:909–916 (1993).

Kumar et al., *Ann. Rev. Immunol.* 7:657–682 (1989).

Lider et al., *J. Autoimmun.* 2:87–99 (1989).

Lider et al., "Anti–Idiotypic Network Induced by T Cell Vaccination Against Experimental Autoimmune Encephalomyelitis." *Science* 239:181–183 (1988).

Link et al., *Neurology* 40(Suppl 1):283 (1990).

Lipoldova et al., *J. Autoimmun.* 2:1–13 (1989).

Londei et al., "Human T–Cell Clones From Autoimmune Thyroid Glands: Specific Recognition of Autologous Thyroid Cells," *Science* 228:85–89 (1985).

MacDonald et al., "T Cell–Receptor V β Use Predicts Reactivity and Tolerance to $MIs^a$–Encoded Genes," *Nature* 332:40–45 (1988).

Margalit et al., Prediction of Immunodominant Helper T Cell Antigenic Sites From the Primary Sequence, *J. Immunol.* 138(7):2213–2229 (1987).

Offner et al., "Lymphocyte Vaccination Against Experimental Autoimmune Encephalomyelitis: Evaluation of Vaccination Protocols," *J. Neuroimmunol.* 21:13–22 (1989).

Offner et al., *J. Exp. Med.* 170:355–367 (1989).

Offner et al., *J. Immunol.* 141(11):3828–3832 (1989).

Offner et al., "T Cell Receptor Peptide Therapy Triggers Autoregulation of Experimental Encephalomyelitis," *Science* 251:430–432 (1991).

Oksenberg et al., "T–Cell Receptor Vα and Cα Alleles Associated with Multiple Sclerosis and Myasthina Gravis," *Proc. Natl. Acad. Sci. USA* 86:988–992 (1989).

Oksenberg et al., *Human Immunol.* 22:111–121 (1988).

Oksenberg et al., "Limited Heterogeneity of Rearranged T-Cell Receptor Vα Transcripts in Brains of Multiple Sclerosis Patients," *Nature* 345:344–346 (1990).

Olsson et al., *J. Clin. Invest.* 86:981–985 (1990).

Ota et al., *Nature* 346:183–187 (1990)1.

Owhashi et al., "Protection From Experimental Allergic Encephalomyelitis Conferred by a Monoclonal Antibody Directed Against a Shared Idiotype on Rat T Cell Receptor Specific for Myelin Basic Protein," *J. Exp. Med.* 168:2153–2164 (1988).

Padula et al., *J. Clin. Invest.* 81:1810–1818 (1988).

Paul (editor), *Fundamental Immunology*, 3rd ed. (1993), pp. 679–685 (Immunological Tolerance), pp. 903–915 (Immunosuppression) and pp. 1033–1095 (Autoimmunity and Autoimmune Disease).

Richert et al., *J. Neuroimmunol.* 23:55–66 (1989).

Rothbard et al., "A Sequence Pattern Common to T Cell Epitopes," *EMBO J.* 7(1):93–100 (1988).

Sakai et al., "Involvement of distinct murine T–cell receptors in the autoimmune encephalitogenic response to nested epitopes of myelin basic protein," *Proc. Natl. Acad. Sci. USA* 85:8608–8612 (1988).

Seboun et al., "A Susceptibility Locus for Multiple Sclerosis is Linked to the T Cell Receptor β Chain Complex," *Cell* 87:1095–1100 (1989).

Sohnle et al., *J. Immunol.* 127(2):612–615 (1981).

Stamenkovic et al., "Clonal Dominance Among T–Lymphcyte Infiltrates in Arthritis," *Proc. Natl. Acad. Sci. USA* 85:1179–1183 (1988).

Stevens et al., "Studies of Vβ8 T Cell Receptor Peptide Treatment in Experimental Autoimmune Encephalomyelitis," *J. Neuroimmunol.* 37:123–129 (1992).

Sun et al., *Europ. J. Immunol.* 18:1993–1999 (1988).

Sun et al., *J. Immunol.* 143:2867–2879 (1989).

Sun et al., "Suppression of Experimentally Induced Autoimmune Encephalomyelitis by Cytolytic T–T Cell Interactions," *Nature* 332:843–845 (1988).

Terasaki et al., "Multiple Sclerosis and High Incidence4 of a B Lymphocyte Antigen," *Science* 193:1245–1247 (1976).

Tuohy et al., *J. Immunol.* 140(6):1868–1873 (1988).

Urban et al., "Restricted Use of T Cell Receptor V Genes in Murine Autoimmune Encephalomyelitis Raises Possibilities for Antibody Therapy," *Cell* 54:577–592 (1988).

Urban et al., *Cell* 59:257–271 (1989).

Vandenbark et al., "Immunization with a synthetic T–cell receptor V–region peptide protects against experimental autoimmune encephalomyelitis," *Nature* 341:541–544 (1989).

Vandenbark et al., "A Myelin Basic Protein–Specific T Lymphocyte Line that Mediates EAE," *J. Immunol.* 135(1):223–228 (1985).

Vandenbark et al., "Dynamic Interactions of Myelin Proteins" pp. 93–108 (1990).

Vandenbark et al., "TCR Peptide Therapy Decreases the Frequency of Encephalitogenic T Cells in the Periphery and the Central Nervous System," *J. Neuroimmunology* 39:251–260 (1992).

Vandenbark et al., "Human T Lymphocyte Response to Myelin Basic Protein: Selection of T Lymphocyte Lines from MPB–Responsive Donor," *J. of Neuroscience Research* 23:21–30 (1989).

Vainiene et al., "Common Sequence on Distinct Vbeta Genes Defines a Protective Iditope in Experimental Encephalomyleitis," *J. of Neuroscience Res.* 31:413–420 (1992).

Waksman et al., *Proc. Soc. Exp. Biol. Med.* 175:282–294 (1984).

Whitman et al., "Suppressor Cell Regulation of Encephalitogenic T Cell Lines: Generation of Suppressor Macrophages with Cyclosporin A and Myelin Basic Protein," *Cell. Immunol.* 126:290–303 (1990).

Williams et al., *Immunol. Res.* 7:339–350 (1988).

Wraith et al., "T Cell Recognition as the Target for Immune Intervention in Autoimmune Disease," *Cell* 57:709–715 (1989).

Wraith et al., *Cell* 59:247–255 (1989).

Wucherpfenning et al., *Science* 248:1016–1019 (1990).

Zamvil et al., "Predominant Expression of a T Cell Receptor V$_\beta$ Gene Subfamily in Autoimmune Encephalomyelitis," *J. Exp. Med.* 167:1586–1596 (1988).

Zamvil et al., *J. Immunol.* 139(4):1075–1079 (1987).

Zamvil et al., "T Cell Clones Sepcific for Myelin Basic Protein Induce Chronic Relapsing Paralysis and Demyelination," *Nature* 317:355–358 (1985).

Zamvil et al., *Nature* 324:258–260 (1986).

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 18 amino acids
( B ) TYPE: amino acid (C) STRANDEDNESS: single
(D) TOPOLOGY: linear (ii) MOLECULE TYPE: peptide (xi) SEQUENCE DESCRIPTION: SEQ ID NO:1:

Pro Lys Ser Gly His Asp Thr Val Ser Trp Tyr Gln Gln Ala Leu Gly
1               5                   10                  15
Gln Gly (2) INFORMATION FOR SEQ ID NO:2:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:2:

Ser Trp Tyr Gln Gln Ala Leu Gly Gln Gly Pro Gln Phe Ile Phe Gln
1               5                   10                  15
Tyr Tyr Glu Glu
            20

(2) INFORMATION FOR SEQ ID NO:3:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

Ala Leu Gly Gln Gly Pro Gln Phe Ile Phe Gln Tyr Tyr Glu Glu Glu
1               5                   10                  15
Glu Arg Gln Arg Gly
            20

(2) INFORMATION FOR SEQ ID NO:4:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:4:

Ala Leu Gly Gln Gly Pro Gln Phe Ile Phe Gln Thr Tyr Glu Glu Glu
1               5                   10                  15
Glu Arg Gln Arg Gly
            20

(2) INFORMATION FOR SEQ ID NO:5:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide ( x i ) SEQUENCE DESCRIPTION: SEQ ID NO:5:

```
Lys Thr Arg Gly Gln Gln Val Thr Leu Arg Cys Ser Pro Lys Ser Gly
1               5                   10                  15
His Asp Thr Val Ser
            20
```

( 2 ) INFORMATION FOR SEQ ID NO:6:

( i ) SEQUENCE CHARACTERISTICS:
       ( A ) LENGTH: 19 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:6:

```
Gln Thr Tyr Glu Glu Glu Glu Arg Gln Arg Gly Asn Phe Pro Asp Arg
1               5                   10                  15
Phe Ser Gly
```

( 2 ) INFORMATION FOR SEQ ID NO:7:

( i ) SEQUENCE CHARACTERISTICS:
       ( A ) LENGTH: 21 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:7:

```
Gly Asn Phe Pro Asp Arg Phe Ser Gly His Gln Phe Pro Asn Tyr Ser
1               5                   10                  15
Ser Glu Leu Asn Val
            20
```

( 2 ) INFORMATION FOR SEQ ID NO:8:

( i ) SEQUENCE CHARACTERISTICS:
       ( A ) LENGTH: 19 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:8:

```
Pro Asn Tyr Ser Ser Glu Leu Asn Val Asn Ala Leu Leu Leu Gly Asp
1               5                   10                  15
Ser Ala Leu
```

( 2 ) INFORMATION FOR SEQ ID NO:9:

( i ) SEQUENCE CHARACTERISTICS:
       ( A ) LENGTH: 9 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:9:

```
Ser Pro Lys Ser Gly His Asp Thr Val
1               5
```

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Gln  Tyr  Tyr  Glu  Glu  Glu  Glu  Arg  Gln  Arg  Gly
  1                  5                       10
```

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Gln  Thr  Tyr  Glu  Glu  Glu  Glu  Arg  Gln  Arg  Gly
  1                  5                       10
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Thr  Pro  Gly  Gln  Gly  Leu  Gln  Phe  Leu  Phe  Glu  Tyr  Phe  Ser  Glu  Thr
  1                  5                       10                       15
Gln  Arg  Asn  Lys  Gly
                 20
```

( 2 ) INFORMATION FOR SEQ ID NO:13:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Val  Leu  Gly  Gln  Gly  Pro  Gln  Phe  Ile  Phe  Gln  Tyr  Tyr  Glu  Lys  Glu
  1                  5                       10                       15
Glu  Arg  Gly  Arg  Gly
                 20
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Glu Tyr Phe Ser Glu Thr Gln Arg Asn Lys Gly
1               5                   10

( 2 ) INFORMATION FOR SEQ ID NO:15:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:15:

Gln Tyr Tyr Gly Lys Glu Glu Arg Gly Arg Gly
1               5                   10

( 2 ) INFORMATION FOR SEQ ID NO:16:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:16:

Ser Pro Ile Ser Gly His Arg Ser Val
1               5

( 2 ) INFORMATION FOR SEQ ID NO:17:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:17:

Ser Pro Ile Ser Gly His Lys Ser Val
1               5

( 2 ) INFORMATION FOR SEQ ID NO:18:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:18:

Ala Leu Gly Gln Gly Pro Gln Phe Ile Phe Gln Tyr Tyr Glu Glu
1               5                   10                  15

( 2 ) INFORMATION FOR SEQ ID NO:19:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:19:

Ala Leu Gly Gln Gly Pro Gln Phe Ile Phe Gln Thr Tyr Glu Glu
1               5                       10                      15

( 2 ) INFORMATION FOR SEQ ID NO:20:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:20:

Pro Lys Ser Gly His Asp Thr Val
1               5

( 2 ) INFORMATION FOR SEQ ID NO:21:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:21:

Pro Ile Ser Gly His Arg Ser Val
1               5

( 2 ) INFORMATION FOR SEQ ID NO:22:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:22:

Leu Phe Glu Tyr Phe Ser Glu Thr Gln Arg Asn Lys Gly Asn
1               5                       10

( 2 ) INFORMATION FOR SEQ ID NO:23:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:23:

Ile Phe Gln Tyr Tyr Glu Glu Glu Arg Gln Arg Gly Asn Phe
1               5                       10                      15

( 2 ) INFORMATION FOR SEQ ID NO:24:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: peptide (xi) SEQUENCE DESCRIPTION: SEQ ID NO:24:

```
Ile Phe Gln Tyr Tyr Glu Lys Glu Glu Arg Gly Arg Gly Asn
 1               5                       10
```

(2) INFORMATION FOR SEQ ID NO:25:

(i) SEQUENCE CHARACTERISTICS:
        (A) LENGTH: 82 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Lys Thr Arg Gly Gln Gln Val Thr Leu Arg Cys Ser Pro Lys Ser Gly
 1               5                       10                  15

His Asp Thr Val Ser Trp Tyr Gln Gln Ala Leu Gly Gln Gly Pro Gln
                20                  25                  30

Phe Ile Phe Gln Tyr Tyr Glu Glu Glu Glu Arg Gln Arg Gly Asn Phe
            35                  40                  45

Pro Asp Arg Phe Ser Gly His Gln Phe Pro Asn Tyr Ser Ser Glu Leu
        50                  55                  60

Asn Val Asn Ala Leu Leu Leu Gly Asp Ser Ala Leu Tyr Leu Cys Ala
65                  70                  75                  80

Ser Ser
```

(2) INFORMATION FOR SEQ ID NO:26:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Leu Gly Gln Gly Pro Glu Phe Leu Ile Tyr Phe Gln Gly Thr Gly Ala
 1               5                       10                  15

Ala Asp Asp Ser Gly
                20
```

(2) INFORMATION FOR SEQ ID NO:27:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Gln Thr Tyr Glu Lys Glu Glu Arg Gly Arg Gly
 1               5                       10
```

1

TCR V BETA 5 PEPTIDES

CROSS-REFERENCE TO RELATED APPLICATIONS

This application is a continuation-in-part of application Ser. No. 08/059,020, filed Mar.16, 1993 now U.S. Pat. No. 5,614,192; which is a file wrapper continuation of Ser. No. 07/735,612, filed Jul. 16, 1991, now abandoned; which is a continuation-in-part of Ser. No. 07/708,022, filed May 31, 1991, now abandoned; which is a continuation-in-part of Ser. No. 07/554,529, filed Jul. 19, 1990, now abandoned; which is a continuation-in-part of Ser. No. 07/467,577, filed Jan. 19, 1990, now abandoned; which is a continuation-in-part of Ser. No. 07/382,804, filed Jul. 19, 1989, now abandoned; all of which are incorporated herein by reference. The application is addressed to subject matter within Group I of the restriction requirement in application Ser. No. 07/735,612.

FIELD OF THE INVENTION

The present invention relates to T cell receptor ("TCR") peptides, particularly to TCR peptides that are useful as therapeutic and/or diagnostic agents, most particularly to to the human TCR peptide family Vβ5, and especially to the human TCR peptide Vβ5.2. The invention is also directed to formulations and methods for treating and diagnosing multiple sclerosis.

BACKGROUND INFORMATION

T cells constitute one of the two branches of the immune system, the cell-mediated branch (antibodies, or humoral-mediated immunity, being the other branch). T cells are specific for their ability to bind to certain foreign proteins (or antigens); the binding takes place when a foreign protein associates with a major histocompatibility complex ("MHC") typically through an antigen presenting cell (or "APC," such as a macrophage) in which the antigen is digested to a smaller-sized fragment and presented on the surface of the APC bound to its MHC.

The TCR is a double stranded protein present on the surface of T cells, the function of which is to recognize and bind with a specific MHC/antigen complex. There are two known types of TCR, TCR2 (composed of an α and a β chain) and TCR1 (composed of a γ and a δ chain). The α and γ chains are each divided into variable ("V"), joining ("J") and constant ("C") regions. The β and δ chains each have V, J and C regions, and also have a diversity ("D") region disposed between V and J. The D region is sometimes shown in parenthesis, e.g., (D), to designate that a diversity region may or may not be present depending on whether the chain is α, β, γ or δ.

Because the individual TCRs are of varying length (particularly in their N-terminus sequences), and given the desirability of designating certain conserved frameworks as having numerically equivalent positions, a variety of numerical nomenclatures have evolved. Widely accepted is the system described by Chothia, et al., *The EMBO J.*, 7(12):3745–3755 (1988) in which the amino acids ("AAs") of the β strand's V region (of particular interest in the present invention) are counted, starting from the conserved cysteine designated as having AA position 92, numerically downward towards the N-terminus. The corresponding conserved cysteine in Vα is designated as having AA position 90.

The selectivity of TCRs is attributable to the numerous combinations of V, (D) and J regions (sometimes collectively referred to as the "variable" region), amplified by random hypervariability (insertion of nucleotides) at the junctions between the genes for the V, (D) and J regions as expressed in their gene products, the TCRs. TCRs have three complementarity determining regions: CDR1 disposed towards the N-terminal of the V region (generally starting at about 2-3 AAs towards the C-terminus from the conserved cysteine at about AA 24 to about 3 AAs towards the N-terminus from the conserved WY framework at about AA 35, e.g., AAs 26-33 of Vβ5.2), CDR2 disposed somewhat in the middle of the V region (generally encompassing the 12th through 25th or 26th AAs towards the C-terminus starting from the conserved WY framework at about AA 35, e.g., about AAs 47-61 of Vβ5.2) and CDR3 disposed across the V(D)J junctions. A fourth such region, CDR4, is reported outside the MHC binding pocket area.

TCR peptides are a sub-genus of T cell-related therapeutic agents, of which everything from complete T cells or complete TCRs, to full α, β, γ or δ chains and peptides from within them have been described. See, e.g., U.S. Pat. Nos. 4,970,296 and 4,886,743, EP 0 340 109 A2, EP 0 479 280 A1, and WO 91/15225. These therapeutic agents have been indicated for the diagnosis and treatment of a variety of immune-related diseases.

Multiple sclerosis ("MS") is an immune-mediated disease characterized by central nervous system mononuclear cell infiltration and demyelination. While the pathogenesis of MS is unknown, both genetic and environmental factors have been implicated in the disease process. Major elements of the genetic predisposition include an association of disease with particular class II MHC halotypes, in particular HLA-DR2 and -DQw1 [Terasaki, et al., *Science*, 193:1245–1247 (1976); Ho, et al., *Immunogenics*, 15:509-517 (1982); Spielman, et al., *Epidemiol. Rev.*, 4:45–65 (1982); Francis, et al., *Lancet*, 1:211 (1986); Elian, et al., *Disease Markers*, 5:89–99 (1987)], as well as with certain polymorphisms within the TCR α chain and β chain gene complexes [Beall, et al., *J. Cell. Biochem.*, 11D:223 (1987); Hauser, et al., *J. Neurol.*, 89:275–277 (1989); Seboun, et al., *Cell*, 57:1095–1100 (1989)]. These studies suggest that the disease involves CD4$^+$T cells bearing an αβ TCR. In support of this idea, CD4$^+$T cells represent a major component of mononuclear cells in the brains of patients with active disease. α/β-chain T cell receptors are present within central nervous system tissue of MS patients but not controls (Terasaki, et al., *Science*, 193:1245–1247 (1976).

T lymphocytes that recognize myelin basic protein (BP) have been shown to have potent demyelinating and encephalitogenic activity in animals (Ben-Nun, et al., *Eur. J. Immunol.*, 11:195–199 (1981); McFarlin, et al., *New. Eng. J. Med.*, 307:1183–1188 (1982); Mokhtarian, et al., *Nature*, 309:356–358 (1984); Vandenbark, et al., *J. Immunol.*, 135:223–228 (1985); Bourdette, et al., *Cell. Immunol.*, 112:351-363 (1988). Accumulating evidence also suggests that BP-specific T cells may contribute to the pathogenesis of MS. Thus, cells selected from MS patients on the basis of in vivo activation have specificity for BP. The frequencies of BP-reactive T cells are also increased in the blood and cerebrospinal fluid (CSF) of MS patents compared to normal individuals or patients with other neurological diseases. Furthermore, recent studies have demonstrated a marked selective enrichment of BP-reactive T cells in the CSF relative to the blood of individual MS patients. In animals, a limited set of TCR α-chain variable (Vα) and β-chain variable (Vβ) genes are utilized by T cells specific for BP [Acha-Orbea, et al. *Cell*, 54:263–273 (1988); Urban, et al., *Cell*, 54:577–592 (1988); Burns, et al., *J. Exp. Med.,*

169:27-39 (1989); Heber-Katz, et al., *Immunol. Today*, 10:164-169 (1989)]. Monoclonal antibodies directed to these regions or synthetic peptides with sequences common to those TCR variable regions can both protect and treat animals with clinical signs of experimental autoimmune encephalomyelitis (EAE) [Acha-Orbea et al, *Cell*, 54:263-273 (1988); Urban et al., *Cell*, 54:577-592 (1988); Vandenbark, et al., *Nature*, 341:541-544 (1989); Howell, et al., *Science*, 245:668-670 (1989)]. In order for a similar approach to be applied to MS patients, it is important to know if potentially pathogenic T cells also preferentially utilize a limited set of V region genes.

As of the original filing in the present series of applications, no effective treatment for MS was known (*Harrison's Principles of Internal Medicine*, 12th ed. Wilson et al., McGraw Hill, Inc. 1991); recently approved have been the drugs IFN-β and COP-1, but additional treatments with greater efficacy are sought. Therapeutic efforts are directed toward amelioration of the acute episode, prevention of relapses or progression of the disease, and relief of symptoms. The clinical manifestations of MS depend upon which nerve group or region of the brainstem, cerebellar or spinal cord is involved. Spinal cord involvement is the predominating feature in most advanced cases of MS.

In acute episodes of disease, glucocorticoid treatment has been suggested as having the potential to lessen the severity of symptoms and speed recovery, however, even its proponents point out that ultimate recovery is not improved by this drug nor is the extent of permanent disability altered. ACTH is the preferred glucocorticoid of clinicians since the only controlled trails which demonstrated any efficacy of glucocorticoid therapy in episodes of MS and optic neuritis were performed with this drug. However, use of long term steroids is not advised.

Immunosuppressive agents such as azathioprine and cyclophosphamide have been claimed to reduce the number of relapses in several series, but there is no consensus about the efficacy of these drugs either.

The current recommendations for the treatment of MS revolve around attempting to avoid exacerbation of the symptoms. Patients are advised to avoid excess fatigue and extremes of temperature and eat a balanced diet. Thus, it remains desired to provide agents and pharmaceutical compositions that have the properties of specificity for the targeted autoimmune response, predictability in their selection, convenience and reproducibility of preparation, and sufficient definition to permit precise control of dosage.

SUMMARY OF THE INVENTION

One aspect of the present invention concerns TCR Vβ5 peptides and functional derivatives thereof. In a preferred aspect, the TCR Vβ5 peptides and functional derivatives comprise an amino acid sequence encompassing at least a part of the second complementarity determining region. In a most preferred aspect, the TCR Vβ 5 peptides and functional derivatives (preferably fragments) are human Vβ5.2, especially Vβ5.2 (25-33), (26-43), (34-53), (47-61) and most especially (39-59).

Particularly preferred peptides and fragments of the invention include:

Vβ5.2 (26-43) - PKSGHDTVSW YQQALGQG (SEQ ID NO:1),

Vβ5.2 (34-53) - SWYQQALGQG PQFIFQYYEE (SEQ ID NO:2),

Vβ5.2 (39-59) - ALGQGPQFIF QYYEEEERQR G (SEQ ID NO:3),

Vβ5.2 (39-59)V - ALGQGPQFIF QTYEEEERQR G (SEQ ID NO:4),

Vβ5.3 (25-33)F - SPISGHKSV (SEQ ID NO:17),

Vβ5.2 (26-33)F - PKSGHDTV (SEQ ID NO:20),

Vβ5.1 and Vβ5.4 (26-33)F - PISGHRSV (SEQ ID NO:21),

Vβ5.1 and Vβ5.4 (47-60)F - LFEYFSETQR NKGN (SEQ ID NO:22),

Vβ5.2 (47-61)F - IFQYYEEEER QRGNF (SEQ ID NO:23), and

Vβ5.3 (47-60)F - IFQYYEKEER GRGN (SEQ ID NO:24).

In another aspect, the invention relates to a pharmaceutical composition containing a therapeutically effective amount of a TCR Vβ5 peptide or functional derivative thereof (particularly as described above) admixed with at least one pharmaceutically acceptable excipient.

In still another aspect, the invention relates to a method of treating multiple sclerosis in a mammal, particularly a human, by administering to a mammal in need of such treatment a therapeutically effective amount of a TCR Vβ5 peptide or functional derivative thereof (particularly as described above), especially Vβ5.2 peptides and functional derivatives, or those of other Vβ5 family members having sufficient similarity to the preferred Vβ5.2 sequence as to retain the activity of the peptide or have advantageous activity, stability or related characteristics.

In yet another aspect, the invention relates to a method of diagnosis for multiple sclerosis by detecting preferential usage of TCR Vβ5 (particularly as described above) in a tissue sample from a mammal, particularly a human, requiring such diagnosis.

DETAILED DESCRIPTION OF THE INVENTION

Definitions, Nomenclature and General Parameters

As used in the present specification, the following words and phrases are generally intended to have the meanings as set forth below, except to the extent that the context in which they are used indicates otherwise.

For purposes of consistency in nomenclature, especially in identification of the peptides and functional derivatives of the present invention, as used herein the amino acids ("AAs") of the β strand's V region are counted, starting from the conserved cysteine designated as having AA position 92, numerically downward towards the N-terminus. Accordingly, Vβ5.2 has the following sequence (in which the first AA is number 14 and the underlined "C" is the conserved cysteine at AA 92):

KTRGQQV TLRCSPKSGH DTVSWYQQAL GQG-PQFIFQY YEEEERQRGN
FPDRFSGHQF PNYSSELNVN ALLLGDSALY LCASS (SEQ ID NO:25).

By "functional derivative" is meant a "fragment," "variant," or "analog" of the peptide, which terms are defined below.

A "fragment" of the peptide of the present invention, refers to any subset of the molecule, that is, a shorter peptide having, e.g., from about 8 to 15 amino acids, preferably from about 9 to about 12 amino acids. Fragments are sometimes indicated by the letter "F" following the AA sequence number designation, e.g., "Vβ5.2 (14-34)F" which is a fragment of Vβ5.2 (10-40).

A "variant" of the peptide refers to a molecule substantially similar to either the entire peptide or a fragment thereof, for example, making amino acid substitutions, preferably conservative substitutions, such that the resulting molecule essentially retains the activity of the peptide or has advantageous activity, stability or related characteristics. Variant peptides may be conveniently prepared by direct chemical synthesis of the variant peptide, using methods well-known in the art. Variants are sometimes indicated by the letter "V" following the AA sequence number designation, e.g., "Vβ5.2 (39-59)V" which in one case is the variant of Vβ5.2 (39-59) where the Y at AA50 is substituted by T.

An "analog" of a peptide refers to a non-natural molecule substantially similar to either the entire molecule or a fragment thereof, for example, making additions or deletions of natural amino acids, and/or making additions and/or substitutions of non-natural amino acids, preferably conservative additions, deletions and/or substitutions (e.g., inserting an alanine or hydroxy-glycine, and substituting D vs. L amino acids) such that the resulting molecule essentially retains the activity of the peptide or has advantageous activity, stability or related characteristics. Analogs are sometimes indicated by the letter "A" following the AA sequence number designation, e.g., "Vβ5.2 (43-59)A" which in one case is the analog of Vβ5.2 (43-59) where the E at AA 53 is deleted.

By the term "protection" from the disease as used herein is intended "prevention," "suppression" or "treatment" of the disease. "Prevention" involves administration of the protective composition prior to the induction of the disease. Thus, for example, in the animal model, EAE, successful administration of a protective composition prior to injection of the encephalitogen that induces the disease results in "prevention" of the disease.

"Suppression" involves administration of the composition after the inductive event but prior to the clinical appearance of the disease. Again, using the EAE example, successful administration of a protective composition after injection of the encephalitogen, but prior to the appearance of neurological symptoms comprises "suppression" of the disease.

"Treatment" involves administration of the protective composition after the appearance of the disease. In the EAE example, successful administration of a protective composition after injection of the encephalitogen and after clinical signs have developed comprises "treatment" of the disease.

"Diagnosis" involves the determination of an individual's susceptibility to, or infection with, a TCR-mediated disease, typically including identification of the TCR bias of that individual.

It will be understood that in human medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

The term "q.s." means adding a quantity sufficient to achieve a stated function, e.g., to bring a solution to the desired volume (i.e., 100%).

Isolation and purification of the peptides described herein can be effected, if desired, by any suitable separation or purification procedure such as, for example, expansion in culture, HPLC, column chromatography, thin-layer chromatography or thick-layer chromatography, or a combination of these procedures.

SYNTHESIS OF THE TCR Vβ5 PEPTIDES

The peptides and functional derivatives of the invention, given their sizes and the disclosure of their sequences, can be prepared according to synthetic and recombinant procedures that are well known in the art, for example synthesis by the Merrifield solid-phase technique and purification by HPLC as described with respect to the "Biological activity of region 65 to 102 of the myelin basic protein" by Hashim, et al., *J. Neurosci. Res.*, 16:467 (1986). Organic solvents employed in the synthesis (e.g., acetonitrile and methanol) are removed, for example by rotary evaporation. Peptide remaining as solute is frozen and lyophilized.

Starting Materials

The materials from which the peptides and functional derivatives of the invention are synthesized are generally commercially available or may be readily prepared by those skilled in the art using commonly employed synthetic methodology.

PREFERRED PEPTIDES

Of the peptides of TCR family Vβ5, preferred are those from Vβ5.2 and the functional derivatives thereof. In a further preferred aspect, the TCR Vβ5 peptides and functional derivatives comprise an amino acid sequence encompassing at least a part of the first or most preferably the second complementarity determining region. In a most preferred aspect, the TCR Vβ5 peptides and functional derivatives (preferably fragments) correspond to human Vβ5.2, especially Vβ5.2 (25-33), (26-43), (34-53), (47-61) especially (39-59).

Specifically preferred are the peptides and functional derivatives:

Vβ5.2 (26-43) - PKSGHDTVSW YQQALGQG (SEQ ID NO:1).

Vβ5.2 (34-53) - SWYQQALGQG PQFIFQYYEE (SEQ ID NO:2).

Vβ5.2 (39-59) - ALGQGPQFIF QYYEEEERQR G (SEQ ID NO:3).

Vβ5.2 (39-59)V - ALGQGPQFIF QTYEEEERQR G (SEQ ID NO:4).

Vβ5.2 (14-34)F - KTRGQQVTLR CSPKSGHDTV S (SEQ ID NO:5).

Vβ5.2 (49-68) - QYYEEEERQR GNFPDRFSG (SEQ ID NO:6).

Vβ5.2 (59-79) - GNFPDRFSGH QFPNYSSELNV (SEQ ID NO:7).

Vβ5.2 (71-89)F - PNYSSELNVN ALLLGDSAL (SEQ ID NO:8).

Vβ5.2 (25-33)F - SPKSGHDTV (SEQ ID NO:9).

Vβ5.2 (49-59)F - QYYEEEERQR G (SEQ ID NO:10).

Vβ5.2 (49-59)FV - QTYEEEERQR G (SEQ ID NO:11).

Vβ5.1 (39-59) and Vβ5.4 (39-59) - TPGQGLQFLF EYFSETQRNK G (SEQ ID NO:12).

Vβ5.3 (39-59) - VLGQGPQFIF QYYEKEERGR G (SEQ ID NO:13).

Vβ5.1 (49-59)F Vβ5.4 (49-59)F - EYFSETQRNK G (SEQ ID NO:14).

Vβ5.3 (49-59)F - QYYEKEERGR G (SEQ ID NO:15).

Vβ5.3 (49-59)FV - QTYEKEERGR G (SEQ ID NO:27).

Vβ5.1 (25-33)F and Vβ5.4 (25-33)F - SPISGHRSV (SEQ ID NO:16).

Vβ5.3 (25-33)F - SPISGHKSV (SEQ ID NO:17).

Vβ5.2 (39-53) - ALGQGPQFIF QYYEE (SEQ ID NO:18).

Vβ5.2 (39-53)V - ALGQGPQFIF QTYEE (SEQ ID NO:19).

Vβ5.2 (26-33)F - PKSGHDTV (SEQ ID NO:20).

Vβ5.1 and Vβ5.4 (26-33)F - PISGHRSV (SEQ ID NO:21).

Vβ5.1 and Vβ5.4 (47-60)F - LFEYFSETQR NKGN (SEQ ID NO:22).

Vβ5.2 (47-61)F - IFQYYEEEER QRGNF (SEQ ID NO:23), and

Vβ5.3 (47-60)F - IFQYYEKEER GRGN (SEQ ID NO:24).

Particularly preferred are the peptides and functional derivatives:

Vβ5.2 (26-43) - PKSGHDTVSW YQQALGQG (SEQ ID NO:1),

Vβ5.2 (34-53) - SWYQQALGQG PQFIFQYYEE (SEQ ID NO:2),

Vβ5.2 (39-59) - ALGQGPQFIF QYYEEEERQR G (SEQ ID NO:3),

Vβ5.2 (39-59)V - ALGQGPQFIF QTYEEEERQR G (SEQ ID NO:4),

Vβ5.3 (25-33)F - SPISGHKSV (SEQ ID NO:17),

Vβ5.2 (26-33)F - PKSGHDTV (SEQ ID NO:20),

Vβ5.1 and Vβ5.4 (26-33)F - PISGHRSV (SEQ ID NO:21),

Vβ5.1 and Vβ5.4 (47-60)F - LFEYFSETQR NKGN (SEQ ID NO:22),

Vβ5.2 (47-61)F - IFQYYEEEER QRGNF (SEQ ID NO:23), and

Vβ5.3 (47-60)F - IFQYYEKEER GRGN (SEQ ID NO:24).

Most preferred are the peptides and functional derivatives:

Vβ5.2 (39-59) - ALGQGPQFIF QYYEEEERQR G (SEQ ID NO:3), and

Vβ5.2 (39-59)V - ALGQGPQFIF QTYEEEERQR G (SEQ ID NO:4).

UTILITY, TESTING AND ADMINISTRATION

General Utility

The peptides of the present invention are useful for the diagnosis and treatment of disease, particularly Vβ5.2 for multiple sclerosis.

Activity Testing and Diagnosis

In vitro activity for TCR peptides and functional derivatives is determined, e.g., by observation of recognition or a related metabolic response upon contact with cultured T cells removed from a mammal susceptible to a particular disease. The recognition and response criteria include proliferation, activation, membrane changes and intracellular changes. This in vitro methodology is also adaptable for disease diagnosis and treatment selection by testing the removed T cells with a panel of TCR peptides and/or functional derivatives known to be associated with a particular disease (such as the established association of certain peptides and functional derivatives of the present invention with multiple sclerosis). Positive recognition/activation results for a peptide or functional derivative known to be associated with a particular disease is indicative of that disease state, whereas negative results (or positive results for a peptide or functional derivative known not to be associated with a suspected disease) indicate otherwise; such positive results also indicate the peptide(s) and/or functional derivative(s) most likely to be successful in treating the disease for that individual. Alternatively, the removed, cultured T cells can be contacted with an autoantigen associated with a particular disease for a time sufficient for autoantigen-induced expansion, followed by isolation of T cells from the expanded clonal sub-set and identification of their TCR bias (e.g., through the use of antibodies), selecting a peptide of the invention corresponding to the identified TCR bias for treatment.

In vivo delayed type hypersensitivity (DTH) skin testing is performed by administering an immunogenic amount of a peptide or functional derivative of the invention by intradermal injection to an individual to be tested, and observing for measurable induration associated with erythema. Positive DTH test results for a peptide or functional derivative known to be associated with a particular disease is indicative of that disease state in a patient suspected of having the disease; such positive results also indicate the peptide(s) and/or functional derivative(s) most likely to be successful in treating the disease for that individual. Negative DTH test results for a peptide or functional derivative known to be indicative of a given disease is of diagnostic value in reducing the likelihood that the patient is suffering from the suspected disease.

Clinical activity for TCR peptides is determined in clinical trials involving patients diagnosed with an immune-related disease, such as multiple sclerosis, preferably in a placebo-controlled, double blinded study.

Administration

The TCR Vβ5 peptides and functional derivatives are administered at a therapeutically effective dosage, e.g., a dosage sufficient to provide treatment for the disease states previously described. Administration of the peptides and functional derivatives of the invention can be via any of the accepted modes of administration for agents that serve similar utilities.

While human dosage levels have yet to be optimized for the peptides and functional derivatives of the invention, generally, a therapeutic dose is from about 10.0 µg to 5.0 mg, preferably about 50 µg to 300 µg, and most preferably about 100.0 µg per dose, administered parenterally (e.g., by intradermal injection), typically with an initial, more frequent basis (such as once a week, e.g., for the first four weeks, followed by once every four weeks thereafter). Dosage adjustment for patient body mass may be undertaken at the discretion of the prescribing physician, given the guideline that TCR peptide therapy dosages do not correlate to body weight to the same degree as do the dosages of active agents of a non-immunogenic nature. Thus, the amount of peptide or functional derivative administered will be dependent on the subject and disease state being treated, the severity of the affliction, the manner and schedule of administration and the judgment of the prescribing physician.

In employing the peptides and functional derivatives of this invention for treatment of the above conditions, any pharmaceutically acceptable mode of administration can be used. The peptides and functional derivatives can be administered either alone or more typically in combination with other pharmaceutically acceptable excipients, including solid, semi-solid, liquid or aerosol dosage forms, such as, for example, tablets, capsules, powders, liquids, suspensions, suppositories, aerosols or the like. The peptides and functional derivatives can also be administered in sustained or controlled release dosage forms, including depot injections, osmotic pumps, pills, transdermal (including electrotransport) patches, and the like, for prolonged and/or timed, pulsed administration at a predetermined rate, preferably in unit dosage forms suitable for single administration of precise dosages. The compositions will typically include a conventional pharmaceutical carrier or excipient. In addition, these compositions may include other medicinal agents, pharmaceutical agents, carriers, adjuvants, and the like. Actual methods of preparing such dosage forms are known, or will be apparent, to those skilled in this art; for example, see *Remington's Pharmaceutical Sciences*, Mack Publishing Company, Easton, Penn., 15th Edition, 1975.

Generally, depending on the intended mode of administration, the pharmaceutically acceptable composition will contain about 0.1% to 90%, preferably about 0.5% to 50% by weight of a peptide or functional derivative of the invention (most preferably for the injectable formulations of the invention 1.0 mg per 1.0 ml), the remainder being suitable pharmaceutical excipients, carriers, and the like.

Parenteral administration is generally characterized by injection, either subcutaneously, intradermally, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

A more recently devised approach for parenteral administration employs the implantation of a slow-release or sustained-release system, such that a constant level of dosage is maintained.

Formulations of the peptides and functional derivatives may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364,838.

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

Preparation of Vβ5 Peptides

By a modification of the Merrifield solid-phase technique and purification by HPLC as described in Hashim, et al., *J. Neurosci. Res.*, 16:467 (1986), there are obtained:

Vβ5.2 (26-43) - PKSGHDTVSW YQQALGQG (SEQ ID NO:1),

Vβ5.2 (34-53) - SWYQQALGQG PQFIFQYYEE (SEQ ID NO:2),

Vβ5.2 (39-59) - ALGQGPQFIF QYYEEEERQR G (SEQ ID NO:3),

Vβ5.2 (39-59)V - ALGQGPQFIF QTYEEEERQR G (SEQ ID NO:4),

Vβ5.2 (14-34)F - KTRGQQVTLR CSPKSGHDTV S (SEQ ID NO:5),

Vβ5.2 (49-68) - QYYEEEERQR GNFPDRFSG (SEQ ID NO:6),

Vβ5.2 (59-79) - GNFPDRFSGH QFPNYSSELNV (SEQ ID NO:7),

Vβ5.2 (71-89)F - PNYSSELNVN ALLLGDSAL (SEQ ID NO:8),

Vβ5.2 (25-33)F - SPKSGHDTV (SEQ ID NO:9),

Vβ5.2 (49-59)F - QYYEEEERQR G (SEQ ID NO:10),

Vβ5.2 (49-59)FV - QTYEEEERQR G (SEQ ID NO:11),

Vβ5.1 (39-59) Vβ5.4 (39-59) - TPGQGLQFLF EYFSETQRNK G (SEQ ID NO:12),

Vβ5.3 (39-59) - VLGQGPQFIF QYYEKEERGR G (SEQ ID NO:13),

Vβ5.1 (49-59)F Vβ5.4 (49-59) - EYFSETQRNK G (SEQ ID NO:14),

Vβ5.3 (49-59)F - QYYEKEERGR G (SEQ ID NO:15),

Vβ5.3 (49-59)FV - QTYEKEERGR G (SEQ ID NO:27),

Vβ5.1 (25-33)F and Vβ5.4 (25-33)F - SPISGHRSV (SEQ ID NO:16),

Vβ5.3 (25-33)F - SPISGHKSV (SEQ ID NO:17),

Vβ5.2 (39-53) - ALGQGPQFIF QYYEE (SEQ ID NO:18),

Vβ5.2 (39-53)V - ALGQGPQFIF QTYEE (SEQ ID NO:19),

Vβ5.2 (26-33)F - PKSGHDTV (SEQ ID NO:20),

Vβ5.1 and Vβ5.4 (26-33)F - PISGHRSV (SEQ ID NO:21),

Vβ5.1 and Vβ5.4 (47-60)F - LFEYFSETQR NKGN (SEQ ID NO:22),

Vβ5.2 (47-61)F - IFQYYEEEER QRGNF (SEQ ID NO:23), and

Vβ5.3 (47-60)F - IFQYYEKEER GRGN (SEQ ID NO:24).

EXAMPLE 2

Purification of Vβ5.2 Peptides

All procedures use filtered water and HPLC-grade acetonitrile. Both water and acetonitrile contain 0.1% trifluoroacetic acid (TFA) as an ion-pairing agent. HPLC columns are Delta Pak C18-300 Å reverse phase columns available from the Waters division of Millipore, Inc.

Crude synthetic peptide is dissolved in water at 5 mg/ml. The pH is adjusted with NaOH as necessary to improve solubility.

A sample is analyzed by reverse phase HPLC using an analytical column (3.9×300 mm) over a gradient of 0 to 100% acetonitrile at a rate of 1% per ml. The profile of a crude synthetic preparation typically contains 10 to 20 peaks, most representing synthetic products with truncated sequences. A target peak representing the putative correct sequence is selected from the analytical profile, and the retention time is noted. The target peak usually comprises between 30% and 70% of the total area of the analytical profile.

The remaining crude synthetic peptide is separated on a preparative column (19×300 mm) and the target peak is collected. Fractions are pooled in a glass flask and sparged with nitrogen for 10 hours to remove acetonitrile and TRA (the removal of which can be tested by sample toxicity to cultured cells). The sparged solution is aliquotted to new sterile 50 ml polypropylene tubes, frozen at −70° C., and lyophilized.

A sample of the lyophilized product is redissolved and analyzed using the analytical column; the measured purity is reported.

By following the above-described procedure, pure Vβ5.2 (39-59)V (SEQ ID NO:4) was obtained.

EXAMPLE 3

TCR Peptide Vβ5 Formulations

Preparation

Purified peptide is weighed in a sterile container. The peptide is then diluted to within 2 to 3 ml of the final volume with Lactated Ringers for Injection. The pH of the resulting solution is tested and adjusted using 1 N NaOH (pharmaceutical grade) to achieve a pH of approximately 7.0. Sufficient Lactated Ringers for Injection is added to provide a final concentration of 1 mg/ml. The solution is then sterilized using a 0.22 micron low protein binding filter into 10 ml empty sterile glass vials. Aliquots (0.3 ml) of the diluted solution are placed into empty sterile 2 ml glass vials. The vials are frozen for storage at −20° C.

Sterility Testinq

Using sterile technique, random aliquots of 5 ml from the diluted peptide prepared as described above is injected into a bottle containing 50 ml of Tsoy broth; 1 ml of the formulation is injected into each of two tubes of thioglycollate broth. The bottle and one tube are incubated at 35° C. The second tube is incubated at 25° C. All are examined for evidence of growth, daily for five days. Any organisms are identified and susceptibility tests are performed as indicated.

Pyrogen Testing

Random aliquots are removed from the diluted peptide prepared as described above. This test solution, adjusted to 37° C., is injected intravenously at 0.7 ml/rabbit via the marginal ear vein. Rectal temperatures are measured electronically in °C. prior to injection (Baseline) and at 30 minute intervals between 1 and 3 hours subsequent to the injection and any pyrexic response noted.

A TCR peptide Vβ5.2 (39-59)V (SEQ ID NO:4) formulation, prepared and tested as described above, gave an acceptable pharmaceutical formulation for injection.

EXAMPLE 4

TCR Peptide Vβ Usage Bias in Multiple Sclerosis Patients

As described in greater detail in Example II of parent application Ser. No. 08/059,020, the specificity of human T cell clones reactive to immunodominant epitopes of myelin basic protein (an antigen associated with the disease process in MS) has been determined from MS patients and normal individuals.

T cell clones were obtained from the blood samples of 11 patients with clinically or laboratory-supported definite MS (7 females and 4 males) and from 9 normal individuals (6 females and 3 males) selected on the basis of positive PBL proliferation responses to human MBP, were phenotyped for the expression of TCR Vβ chain gene products using mouse monoclonal antibodies specific for human TCR Vβ. $2\times10^5$ T cells were incubated with 5 µl of each antibody for 1 hour at 4° C., followed by 3 washes with medium containing 5% human AB serum and further incubation with FITC-conjugated goat anti-mouse IgG for 30 min. After 2 washes and fixation in 2% formaldehyde, the stained cells were evaluated for immunofluorescence using a FACScan flow cytometer as follows.

| Donor | # Clones | Vβ Genes Use |
|---|---|---|
| MS-1 | 13 | 5.2 |
| MS-1 | 1 | 5.1 |
| MS-2 | 4 | 5.2 |
| MS-2 | 1 ea. | 3, 4, 6, 9 |
| MS-3 | 1 | 5.2 |
| MS-4 | 1 | 6 |
| N-1 | 12 | 14 |
| N-2 | 1 | 2 |

Similarly, in a different set of MS Donors, Vβ gene usage for Vβ3, Vβ5.2, Vβ6.1, Vβ9, Vβ12.2, Vβ13.1 and Vβ15 was identified.

EXAMPLE 5

Successful Immunization of Patients with Synthetic Vβ5.2 and Vβ6.1 CDR2 Peptides The following is excerpted from Bourdette, et al., *J. Immunol.*, 152:2510 (1994) reporting the results of a clinical trial conducted in accordance with the teachings of the present invention by colleagues of the inventor.

Subjects

Nine men and two women with clinically or laboratory-supported definite MS by Poser criteria participated. Ten of the patients had chronic progressive disease and one had relapsing/progressive MS. The patients had a mean age of 52 (range, 37 to 66 years), mean duration of MS of 18 years (range, 7 to 30 years), and mean Kurtzke expanded disability status score (EDSS) of 6.0 (range, 3.5 to 7.5). TCR V gene usage of MBP-specific T cell clones from three of the patients had been determined previously as follows:

| Patient | Vβ5.2 | Vβ6.1 |
|---|---|---|
| M. R. | 4/10 | 2/10 |
| N. L. | 13/14 | 0/14 |
| W. S. | 3/6 | 2/6 | while TCR V gene usage was not known for the remaining patients.

Immunization

Patients received varying dosages of peptides Vβ5.2 (39-59)V (SEQ ID NO:4) and Vβ6.1 (39-59) - LGQGPE-FLIYFQGTGAADDSG (SEQ ID NO:26), intradermally in the forearm in 0.1 to 0.3 ml volumes at one or two sites in concentrations of 1 or 5 mg/ml. When starting a peptide, patients initially received four weekly injections of 100 µg (0.1 ml of 1 mg/ml). Patients then received injections every 4 weeks thereafter with dosages being incrementally increased. Doses administered were 100, 200, 300, 600, 1500 and 3000 µg. Both peptides were tested in three patients at the maximum dose of 3000 µg. The maximum dosage given to the remaining patients varied. After completing dosage escalation with the first peptide, patients were started on the second peptide with or without the first peptide being continued. Five patients initially received Vβ5.2 (39-59)V and six initially received Vβ6.1 (39-59).

Delayed type hypersensitivity (DTH) skin reactions

DTH skin reactions were monitored 24 to 48 hours after each intradermal rejection. A skin reaction was considered positive if there was any measurable induration associated with erythema of 10 mm or greater; erythema alone was not regarded as a positive DTH response.

DTH skin reactions occurred in two of six responders to Vβ5.2 (39-59)V and in two of six responders to Vβ6.1 (39-59). For both peptides, DTH skin responses occurred in the patients with the highest mean peptide-specific T cell frequencies and tended to occur when T cell frequencies were $>8\times10^{-6}$. One patient (K. J.) had a measurable DTH skin response to the Vβ6.1 beginning with the third injection and recurring with every injection thereafter; the response was maximal 24 to 48 hours after injection, and the magnitude of induration varied between 6 and 30 mm. This patient had skin responses to the Vβ5.2, although they were less consistent and vigorous than that patient's responses to Vβ6.1. DTH responses of the other patients occurred less frequently, but when responses developed, the temporal pattern and size of induration were similar to those of K. J.

Punch biopsies of the injection sites from one patient were obtained 24 hours after administration of Vβ5.2 (39-59)V and Vβ6.1 (39-59). The biopsies were frozen and paraffin-embedded sections were stained with hematoxylin-eosin and immunostained for CD3 (pan T cell marker), CD4 (helper/inducer T cell marker), and CD8 (suppressor/cytotoxic T cell marker). The routine histologic staining disclosed intradermal perivascular mononuclear inflammatory cells. The immunohistochemical staining revealed these cells to be principally CD3⁺T cells with an estimated ratio of CD4⁺:CD8⁺T cells of 2:1. These pathologic findings were consistent with a cell-mediated immune reaction.

Clinical Results

Twelve months after the initiation of TCR peptide immunization, a determination was made as to whether each patient was worse, stable or improved. Among the seven peptide responders, two were improved, three were stable, and two were worse. Among the four peptide nonresponders no one was improved, all four were worse.

EXAMPLE 6

TCR Peptide Vβ5 Treatment of Multiple Sclerosis

A double blinded, randomized placebo controlled trial is conducted in patients who have relapsing progressive or chronic progressive MS and who are HLA-DR2⁺. One-third of the randomized patients are assigned to the placebo group, the other two-thirds of the randomized patients are treated with test peptide. Once randomized, patients receive 0.1 ml (containing 100 μg of test peptide or placebo) intradermally once a week for 4 weeks and then once every 4 weeks thereafter. Study duration is 1 year.

Clinical Evaluation

A patient history is obtained and an examination is performed at time of entry and at weeks 12, 26, 39 and 52.

Each patient is evaluated at entry and at weeks 26 and 52, assigning to the patient scores on the Expanded Disability Status Scale (EDSS—a measure of disability based on 6 sub-scales) and on the Ambulation Index (AI—assessing ambulation based on a timed 25 foot walk) [Kurtzke, *Neurology*, 33:1444–1452 (1983); and Hauser et al., *N. Engl. J. Med.*, 308:173–180 (1983)]. Each examination is without reference to previous scores.

Each patient is evaluated on three separate occasions during the 1–2 weeks prior to time of entry and at weeks 12, 26, 39 and 52 by the 9-Hole Peg Test (9-HPT) and the Box and Block Test (B&BT), which measure hand dexterity [Goodkin, et. al., *Arch. Phys. Med. Rehabil.*, 69:850–854 (1988)].

An increase in EDSS by ≧ 1.0 for patients with a baseline EDSS of ≦ 5.5, or an increase of ≧ 0.5 for patients with a baseline of EDSS of 6.0–6.5 is classified as a treatment failure. Significant worsening (change greater than 2 standard deviations from the mean of the baseline value) on the timed 25 foot walk, 9-HPT or B&BT, maintained for at least 3 months is classified as a treatment failure.

Evaluation of Changes in Antigen Specific Immunity

Using a limited dilution assay, the frequency of BP and TCR peptide specific T cells in blood of patients is assessed. Two pre-treatment values are obtained within 4 weeks of entry into the trial. Frequencies are determined 4 and 5 weeks after the first treatment, and at weeks 8, 12, 24, 40 and 52. Serum samples obtained at the same time are assayed for the presence of anti-TCR peptide specific antibodies, using an ELISA.

Patients who have 2 or more consecutive T cell frequencies to the test peptide that are significantly higher than their pre-immunization frequency are classified as peptide responders. Patients having two significant decreases in T cell frequencies to BP, compared to their pre-immunization frequency, are be classified as having a significant decrease.

Safety Analysis

Renal and/or hepatic toxicity is evaluated by blood chemistry and electrolytes. Hematologic toxicity is evaluated by CBC. Evidence of allergic reactions is evaluated by clinical examination. Neurologic status is evaluated by clinical exam.

Results

A group of 23 HLA-DR2⁺ patients who have relapsing progressive or chronic progressive MS are being tested, receiving TCR peptide Vβ5.2 (39-59) in accordance with the above-described protocol. A preliminary comparison has been made of 9 patients assessed for immune response to the peptide (measured marked, moderate or weak/none) and clinical outcome, the immunologic responsiveness (patients scored as improved, stable or worse) in blinded fashion by physicians unaware of immunological responsiveness. The patient with highest immunological responsiveness to the therapy was rated as improved. Patients with moderate immune response were rated as stable. Patients with no/weak response were rated as stable or worse. The 2 patients who received placebo (determined by another individual having access to the code) were rated as stable or worse.

The one of the 9 patients who have completed the study (having the marked response to peptide and improved physician evaluation) has been followed for 6 months after study completion (and has continued on drug for 1.5 years) —drop in EDSS score from 6 to 5 at 12 month point and down to 4.5 at 18 months. Immunological response to MBP inversely correlated to response to peptide. This patient is reported to no longer require walking aids.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

---

What is claimed is:

1. A purified or synthetic immunogenic T cell receptor peptide capable of reducing the severity of a T cell mediated disease, selected from the Vβ5 family, having an amino acid sequence of about 15 to 30 amino acid comprising at least part of the second comlementarity determing region of a T cell tor characteristic of such T cell mediated disease, or a corresponding purified or synthetic immunogenic functional derivative that is a fragment, a variant or an analog of said peptide.

2. The T cell receptor peptide or functional derivative of claim 1 which is a fragment having an amino acid sequence that overlaps said second complementarity determining region.

3. The T cell receptor peptide or functional derivative of claim 1 consisting of an amino acid sequence entirely within said second complementarity determining region.

4. The T cell receptor peptide or functional derivative of claim 1 wherein said amino acid sequence consists essentially of the entire second complementarity determining region.

5. The T cell receptor peptide or functional derivative of claim 1 which is a Vβ5.1 or Vβ5.2.

6. A peptide selected from the group consisting of:

Vβ5.2 (34-53) - SWYQQALGQG PQFIFQYYEE (SEQ ID NO:2),

Vβ5.2 (39-59) - ALGQGPQFIF QYYEEEERQR G (SEQ ID NO:3),

Vβ5.2 (39-59)V - ALGQGPQFIF QTYEEEERQR G (SEQ ID NO:4),

Vβ5.2 (49-68) - QYYEEEERQR GNFPDRFSG (SEQ ID NO:6),

Vβ5.2 (49-59)F - QYYEEEERQR G (SEQ ID NO:10),

Vβ5.2 (49-59)FV - QTYEEEERQR G (SEQ ID NO:11),

Vβ5.3 (39-59) - VLGQGPQFIF QYYEKEERGR G (SEQ ID NO:13),

Vβ5.3 (49-59)F - QYYEKEERGR G (SEQ ID NO:15),

Vβ5.2 (39-53)V - ALGQGPQFIF QTYEE (SEQ ID NO:19), and

Vβ5.2 (47-61)F - IFQYYEEEER QRGNF (SEQ ID NO:23).

7. The peptide of claim 6 selected from the group consisting of:

Vβ5.2 (34-53) - SWYQQALGQG PQFIFQYYEE (SEQ ID NO:2),

Vβ5.2 (39-59) - ALGQGPQFIF QYYEEEERQR G (SEQ ID NO:3), and

Vβ5.2 (39-59)V - ALGQGPQFIF QTYEEEERQR G (SEQ ID NO:4).

8. The T cell receptor peptide of claim 1 that is Vβ5.2 (39-59) - ALGQGPQFIF QYYEEEERQR G (SEQ ID NO:3).

9. The peptide of claim 7 that is Vβ5.2 (39-59)V - ALGQGPQFIF QTYEEEERQR G (SEQ ID NO:4).

10. A pharmaceutical formulation comprising a therapeutically effective amount of the T cell receptor peptide or functional derivative of claim 1 and a pharmaceutically acceptable excipient.

11. A pharmaceutical formulation comprising a therapeutically effective amount of the T cell receptor peptide or functional derivative of claim 5 and a pharmaceutically acceptable excipient.

12. A pharmaceutical formulation comprising a therapeutically effective amount of the peptide of claim 6 or an amount sufficient for DTH testing and a pharmaceutically acceptable excipient.

13. A pharmaceutical formulation comprising a therapeutically effective amount of the T cell receptor peptide of claim 8 and a pharmaceutically acceptable excipient.

14. A pharmaceutical formulation comprising a therapeutically effective amount of the peptide of claim 9 or an amount sufficient for DTH testing and a pharmaceutically acceptable excipient.

15. The pharmaceutical formulation of claim 10 comprising said peptide or functional derivative at a concentration of about 1 mg/ml in lactated ringers for injection.

16. The pharmaceutical formulation of claim 13 comprising said peptide at a concentration of about 1 mg/ml in lactated ringers for injection.

17. The pharmaceutical formulation of claim 14 comprising said peptide. functional derivative at a concentration of about 1 mg/ml in lactated ringers for injection.

18. The functional derivative of claim 1 that is a fragment.

19. The functional derivative of claim 1 that is an analog.

20. The functional derivative of claim 1 that is a variant.

21. A pharmaceutical formulation comprising:

one or a combination of purified or synthetic immunogenic T cell receptor peptides of the Vβ5 family, having an amino acid sequence of about 15 to 30 amino acids, each comprising an amino acid sequence comprising at least a part of the second complementarity determining region of a T cell receptor characteristic of a T cell mediated disease disease; or one or a combination of corresponding purified or synthetic immunogenic functional derivatives. comprising a fragment, a variant or an analog of a said peptide; or a combination of one or more of said peptides and one or more of said functional derivatives, present in an amount effective to reduce the severity of a T cell mediated disease, and a pharmaceutically acceptable excipient.

22. A method for reducing the severity of a T cell mediated disease by administering to a mammal in need thereof an effective amount of a purified or synthetic immunogenic T cell receptor peptide comprising an amino acid sequence of about 15–30 amino acids encompassing at least a part of the second complementarity determining region of a Vβ5 T cell receptor characteristic of the disease, or administering an effective amount of a corresponding purified or synthetic immunogenic functional derivative that is a fragment, a variant or an analog of said peptide.

23. The method of claim 22 wherein the T cell receptor is of human origin.

24. The method of claim 22 wherein said functional derivative comprises an amino acid sequence that overlaps said second complementarity determining region.

25. The method of claim 22 wherein said T cell receptor is selected from human Vβ5.1 or human Vβ5.2.

26. The method of claim 22 wherein said purified T cell receptor peptide or functional derivative is selected from the group consisting of:

Vβ5.2 (39-59) - ALGQGPQFIF QYYEEEERQR G (SEQ ID NO:3), and

Vβ5.2 (39-59)V - ALGQGPQFIF QTYEEIEERQR G (SEQ ID NO:4).

27. The method of claim 22 comprising injecting a human immune-related disease-sufferer with about 0.1 ml of a pharmaceutical formulation containing said peptide or functional derivative at a concentration of about 1 mg/ml.

* * * * *